United States Patent
Hedberg (10) Patent No.: US 10,457,905 B2
(45) Date of Patent: Oct. 29, 2019

(54) BIOREACTOR CONNECTORS

(71) Applicant: Biostage, Inc., Holliston, MA (US)

(72) Inventor: Herbert Hedberg, Holliston, MA (US)

(73) Assignee: Biostage, Inc., Holliston, MA (US)

( * ) Notice: Subject to any disclaimer, the term of this patent is extended or adjusted under 35 U.S.C. 154(b) by 0 days.

(21) Appl. No.: 14/775,085

(22) PCT Filed: Mar. 15, 2014

(86) PCT No.: PCT/US2014/030030
§ 371 (c)(1),
(2) Date: Sep. 11, 2015

(87) PCT Pub. No.: WO2014/145292
PCT Pub. Date: Sep. 18, 2014

(65) Prior Publication Data
US 2016/0040107 A1    Feb. 11, 2016

Related U.S. Application Data

(60) Provisional application No. 61/791,950, filed on Mar. 15, 2013.

(51) Int. Cl.
*C12M 3/00* (2006.01)
*C12M 1/12* (2006.01)

(52) U.S. Cl.
CPC ............ *C12M 21/08* (2013.01); *C12M 23/04* (2013.01); *C12M 23/06* (2013.01); *C12M 25/14* (2013.01)

(58) Field of Classification Search
CPC ...... C12M 21/08; C12M 23/06; C12M 25/10; C12M 25/12; C12M 25/14; C12M 27/14
See application file for complete search history.

(56) References Cited

U.S. PATENT DOCUMENTS

| | | | | |
|---|---|---|---|---|
| 4,546,500 A | * | 10/1985 | Bell | A61F 2/022 435/1.1 |
| 4,908,013 A | * | 3/1990 | Muller | A01N 1/02 435/1.1 |
| 6,416,995 B1 | * | 7/2002 | Wolfinbarger | A61F 2/062 435/284.1 |
| 2006/0075963 A1 | * | 4/2006 | Nieponice | A61F 2/062 118/417 |

* cited by examiner

*Primary Examiner* — William H. Beisner
(74) *Attorney, Agent, or Firm* — Young Basile Hanlon & MacFarlane, P.C.

(57) ABSTRACT

Aspects of the disclosure relate to rotating bioreactors and articles and methods that are useful for adapting a rotating bioreactor for use with tissues or scaffolds of different sizes. In some embodiments, bioreactors comprising a reservoir and an arbor assembly are provided herein, in which the arbor assembly comprises a rotatable support to which a tissue or tissue scaffold can be attached.

6 Claims, 7 Drawing Sheets

BIOREACTOR CONNECTORS

RELATED APPLICATIONS

This Application is a national stage entry of PCT/US2014/030030 filed on Mar. 14, 2014 which claims priority under 35 U.S.C. § 119 (e) to U.S. Provisional Application Ser. No. 61/791,950, entitled "BIOREACTOR CONNECTORS" filed on Mar. 15, 2013, which is herein incorporated by reference in its entirety.

BACKGROUND

Engineered tissues or organs can be produced ex vivo (for example in a bioreactor) and implanted into a host (e.g., a human patient) in order to replace or supplement an injured, diseased, or otherwise failing organ in the host. Engineered tissues or organs can be produced in a bioreactor by cellularizing a support structure referred to as a scaffold. Current techniques for producing scaffolds that can be cellularized ex vivo include methods that involve decellularizing a natural organ or tissue to produce an acellular scaffold of natural structural material, or methods that involve configuring a synthetic material to mimic a shape of a natural scaffold.

SUMMARY

Aspects of the disclosure relate to rotating bioreactors and articles and methods that are useful for adapting a rotating bioreactor for use with tissues or scaffolds of different sizes. Bioreactors described herein can be used for decellularizing a tissue and/or for seeding cells onto natural or synthetic scaffold structures, and/or for conditioning scaffolds, patches, tubes, or other natural or synthetic material (e.g., that is conditioned to increase compatibility with cells or tissue that are contacted with or grown on the material). Accordingly, in some embodiments the present disclosure relates generally to articles and methods for growing tissues and organs, and, more specifically, to growing tissues and organs using rotating bioreactors. In some embodiments, the present disclosure relates to conditioning articles, for example by coating them with a biocompatible material (e.g., a proteinaceous material, for example, extracellular material). In some embodiments, the articles and methods can be used to form biocompatible structures for tissue engineering and organ replacement.

In some embodiments, bioreactors comprising a reservoir and arbor assembly are provided herein. Accordingly, in some embodiments, a bioreactor arbor assembly is provided in which the arbor assembly acts as a support to which a tissue or tissue scaffold can be attached, thereby allowing the tissue or tissue scaffold to be rotated within a fluid in the reservoir of a bioreactor. In some embodiments, the arbor assembly comprises i) a first cylindrical end and a second cylindrical end, in which the first and second cylindrical ends are connected via an elongate member, ii) a first cannula unit connected to the first end, and iii) a second cannula unit connected to the second end. In some embodiments, the first and second cannula units are connected via threaded screws onto the first and second ends. In some embodiments, a spacer unit is positioned between the first cannula and the first end. In some embodiments, a first opening of a tubular scaffold is attached to the first cannula and a second opening of a tubular scaffold is attached to the second cannula. In some embodiments, the elongate member is a shaft. In some embodiments, the two cylindrical ends confront one another. In some embodiments, the first cannula unit comprises an orifice and the second cannula unit comprises an orifice, wherein the first and second cannula units are arranged such that they confront one another along a longitudinal axis that passes through the two orifices.

DETAILED DESCRIPTION

Aspects of the disclosure relate to rotating bioreactors and articles and methods that are useful for adapting a rotating bioreactor for use with tissues or scaffolds of different sizes. Bioreactors described herein can be used for decellularizing a tissue and/or for seeding cells onto natural or synthetic scaffold structures and/or for conditioning natural or synthetic material for use with tissue or cellular material. In some embodiments, the present disclosure relates generally to articles and methods for growing tissues and organs, and, more specifically, to growing tissues and organs using rotating bioreactors. In some embodiments, the articles and methods can be used to form biocompatible structures for tissue engineering and organ replacement. The subject matter of the present invention involves, in some cases, inter-related products, alternative solutions to a particular problem, and/or a plurality of different uses of one or more systems and/or articles.

In some embodiments, a bioreactor comprises a housing with a reservoir (see FIG. 1 for example) and an arbor assembly (see FIG. 2 for example) that can be placed in the reservoir and connected to a drive shaft that can be used to rotate the arbor assembly around a longitudinal axis within the reservoir. The arbor assembly acts as a support to which a tissue or tissue scaffold can be attached, thereby allowing the tissue or tissue scaffold to be rotated within a fluid in the reservoir. In some embodiments, the arbor includes a cannula at each end that can be used to attach to each end of a tubular tissue or scaffold to form a fluid pathway that allows fluid to be passed through (e.g., pumped through) the lumen of the tissue or scaffold. In some embodiments, the fluid in the lumen is different from the fluid in the reservoir. Accordingly, two separate fluid pathways can be used independently and connected (e.g., via appropriate tubing) to separate external reservoirs and/or pumps in some embodiments. However, it should be appreciated that the same fluid can be used in both pathways in some embodiments, as described in more detail herein.

Figure 1:
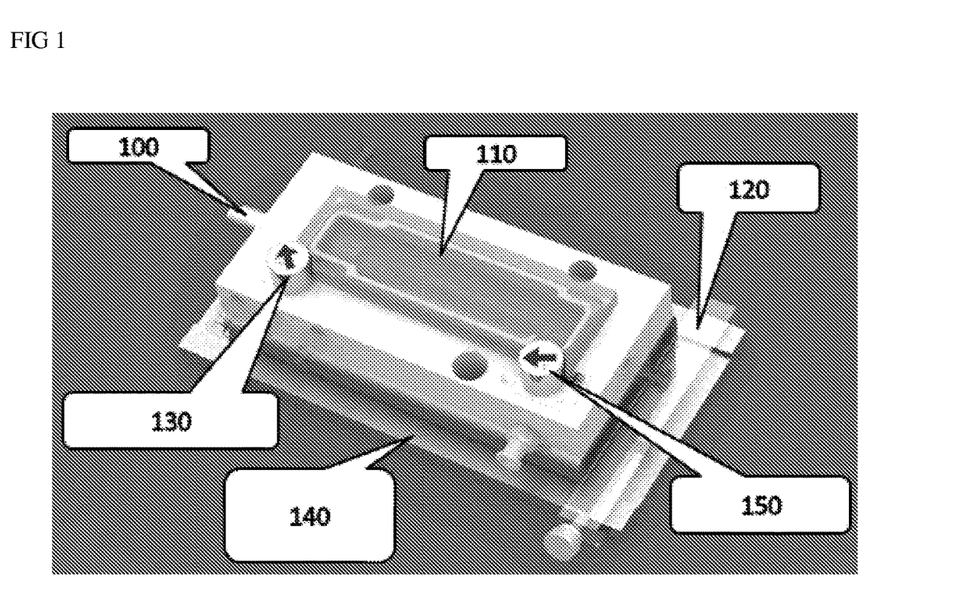
FIG. 1 depicts a non-limiting embodiment of a bioreactor comprises a housing with a reservoir.

It should be appreciated that the arbor assembly can be placed horizontally within a reservoir as illustrated in FIG. 1. However, in other embodiments a bioreactor can be configured such that the arbor is place vertically within the bioreactor and the opening of the bioreactor is at one end of the arbor (e.g., with the lid placed over one end of the arbor) as aspects of the disclosure are not limited in this respect.

In some embodiments, the disclosure relates to articles and methods for adjusting the end-to-end length between the cannulae on the arbor. In some embodiments, the disclosure relates to articles and methods for adjusting the outer diameter of the cannula at each end of the arbor. These features allow a bioreactor described herein to be used with tubular tissues and/or synthetic or natural scaffolds having different lengths and inner diameters.

In some embodiments, a bioreactor described herein can be used to decellularize a tubular tissue (e.g., a natural trachea). In some embodiments, a bioreactor described herein can be used to condition and/or recellularize a synthetic or natural scaffold (e.g., to produce a synthetic airway that can be implanted into a subject, for example a human subject). In some embodiments, scaffolds are formed as tubular structures that can be seeded with cells to form tubular tissue regions (e.g., tracheal, bronchial, or other tubular regions). It should be appreciated that a tubular region can be a cylinder with a uniform diameter. However, in some embodiments, a tubular region can have any appropriate tubular shape (for example, including portions with different diameters along the length of the tubular region). A tubular region also can include a branch or a series of branches. In some embodiments, a tubular scaffold is produced having an opening at one end, both ends, or a plurality of ends (e.g., in the case of a branched scaffold). However, a tubular scaffold may be closed at one, both, or all ends, as aspects of the invention are not limited in this respect. It also should be appreciated that aspects of the invention may be used to produce scaffolds for any type or organ, including hollow and solid organs, as the invention is not limited in this respect. In some embodiments, aspects of the invention are useful to enhance cellularization of a tubular scaffold that includes an opening at each end. In some embodiments, a scaffold is a natural scaffold obtained from a decellularized tissue. In some embodiments, a scaffold is a synthetic scaffold produced from electrospun, molded, cast, or other synthetic or polymeric material, or a combination thereof.

In some embodiments, a bioreactor described herein is a rotating, double chamber bioreactor designed for cell seeding and culturing of both surfaces of a tubular scaffold. In some embodiments, chambers of a bioreactor are defined by a scaffold that is placed between the two opposing cannulae, in which the space inside the scaffold is the inner chamber (or a portion of the inner chamber) and the space outside the scaffold bounded by the reservoir is the outer chamber (or part of the outer chamber). In some embodiments, the bioreactor allows rotational movement of the scaffold around its longitudinal axis. In some embodiments, a polymeric chamber houses the biological materials throughout the culture period. In some embodiments, cylindrical scaffold holders are constructed with working ends of different diameters—to support scaffold of different dimensions— and a central portion of smaller diameter to expose the luminal surface of the scaffold for cell seeding and culturing.

In some embodiments, a co-axial conduit links the inner chamber to the external environment through the chamber wall. This provides access to provide solutions that are useful for seeding and feeding the luminal surface of a construct. In some embodiments, secondary elements moving with the scaffold holder induce continuous mixing of the culture medium to increase oxygenation and mass transport. In some embodiments, secondary elements moving with the scaffold can be used to transport fluid (e.g., a growth medium or cellular solution) from an inner chamber to an outer chamber, from an outer chamber to an inner chamber, from a reservoir to an inner or outer chamber, or to distribute fluid over the surface of the scaffold (for example by collecting it from the outer chamber and depositing over the rotating surface (e.g., outer surface) of the scaffold.

In some embodiments, a bioreactor described herein is used in combination with a drive motor base plate that aligns the reservoir with the drive motor, a control unit that provides an independent controller of rotational speed (however, other controllers can be used); and a motor drive that is responsible for rotating arbor and scaffold. However, it should be appreciated that different drive configurations may be used to connect the scaffold support to the drive motor including mechanical and/or electromagnetic connections between the arbor (e.g., including a driveshaft) and a motor and/or including magnetic and/or electromagnetic bearings.

FIG. 1 illustrates a non-limiting embodiment of a bioreactor (cover not shown). A driveshaft (100) connects the shaft that links the motor to the arbor allowing for rotational control. A reservoir (110) provides a cavity within which the arbor and scaffold can be placed within a volume of reagent and/or medium. A retainer clamp (120) can be used to clamp the reactor to a solid surface (e.g., a table or other solid surface). A function control valve (130) allows selection of multiple flow paths described in more detail herein. A drive motor base plate (140) aligns the reservoir with the drive motor (e.g., electrical motor, servo motor, etc.) or other suitable driver. A level control valve (150) allows the level of the medium in the reservoir to be controlled.

The function control valve allows several flow paths to be selected. In a first position, the lumen flow is blocked. In some embodiments, this allows pressure to be increased within the lumen of the scaffold. In a second position, the lumen flow is connected to the lumen flow outlet so that the medium/reagent can be removed from the reactor. In a third position, lumen flow is re-circulated into the reservoir.

In some embodiments, a valve of the disclosure comprises a cavity (e.g., well, hole, recess) within the body (housing) of the bioreactor (e.g., integral to the wall of the reservoir) and a valve element that is adapted to fit into the cavity. The valve element may be configured with a rotatable member (e.g., cylinder) with one or passages that direct flow through the body (e.g., into or out from the reservoir). In some embodiments, the valve element may be configured with a rotatable member (e.g., cylinder) with one or passages that direct flow through the body, such that in one rotated position the valve is closed and prevents flow through the body and in another rotated position the valve element defines a passage (e.g., inlet or outlet passage) that provides fluid communication with the reservoir. In certain positions, fluid flow occurs when a passage within the body of the valve element lines up with passages within the body of the bioreactor (e.g., within the wall of the reservoir) that are connected to the reservoir or other fluid inlets or outlets as described herein. In some embodiments, fluid flow does not occur when the valve element is positioned (e.g., rotated) such that at least one end of a passage through the body of the valve element does not line up with a passage in the body of the bioreactor. Accordingly, different valve elements can be used to control the fluid connection between different flow paths and chamber within a bioreactor.

Figure 2:
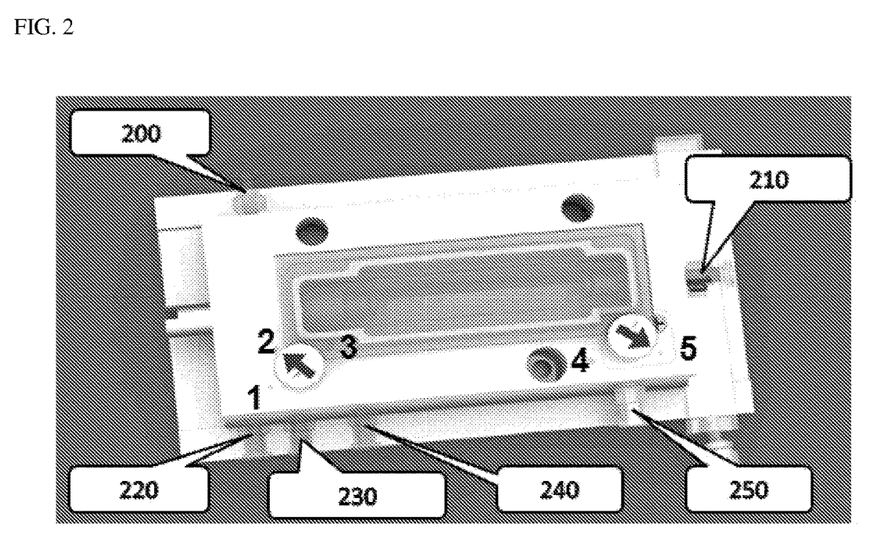
FIG. 2 depicts a non-limiting embodiment of a bioreactor.

FIG. 2 illustrates a non-limiting embodiment of a bioreactor showing non-limiting embodiments of a seal wash inlet (200), a lumen flow inlet (210), a seal wash outlet (220), a lumen flow outlet (230), a reservoir inlet (240), and a reservoir outlet (250).

Figure 3:
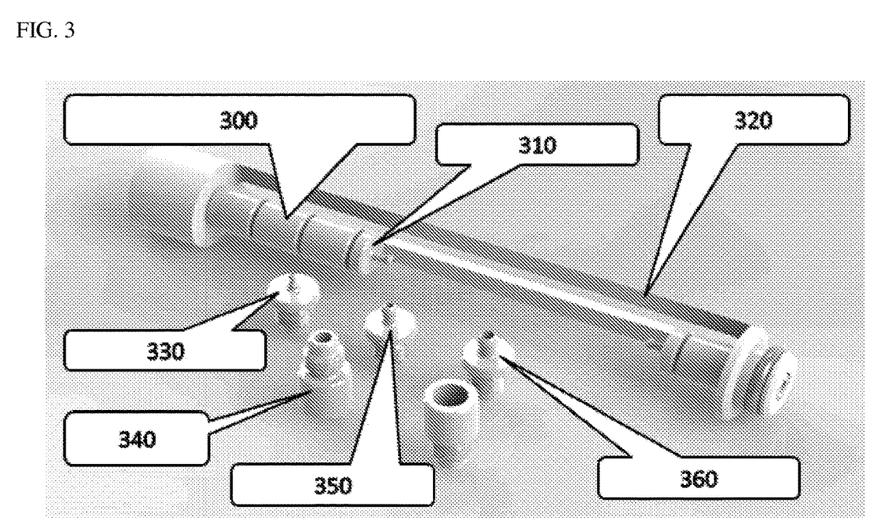
FIG. 3 illustrates a non-limiting embodiment of a bioreactor arbor assembly.

FIG. 3 illustrates a non-limiting embodiment of an arbor assembly showing non-limiting embodiments of spacers (300) that are attached to a first end of the arbor assembly to reduce cannula-to-cannula distance, an exposed cannula (310) onto which a scaffold can be attached, an arbor (320) that connects the two ends of the arbor assembly, examples of a stackable spacer (340) and cannulas of different sizes (330, 350, and 360). In some embodiments, an arbor assembly includes a first end (e.g., a first cylindrical end) that is adapted to connect to the drive shaft, and a second end (e.g., a second cylindrical end) that is adapted to fit in a pocket at an end of the reservoir adjacent to the lumen flow inlet in order to form a fluid connection with the fluid flow inlet. In some embodiments, the first and second ends of the arbor are separated by a connector rod (e.g., one or more connector rods) that determine the distance between the first and second ends. In some embodiments, the one or more connector rods are located away from the central axis of the arbor assembly to avoid interfering with the scaffold or tissue that is connected to the cannulae. In some embodiments, two connector rods are included to provide increased rigidity. In some embodiments, two connector rods are adjacent to each other on the arbor end pieces. In some embodiments, two connector rods are approximately diametrically opposite each other on opposite sides of the arbor end pieces. However, other configurations can be used as aspects of the disclosure are not limited in this respect. Connector rods can be metal and/or polymeric rods, or made of any other suitable material.

In some embodiments, a cannula is provided at each end of the arbor so that each end of a tubular scaffold (e.g., a synthetic or natural scaffold being recellularized) or tissue (e.g., an airway tissue being decellularized) can be attached to a cannula and connected to the intralumenal flow path. In some embodiments, one or both cannulae are provided as units that can be detached form the arbor (e.g., using a threaded screw fitting to the arbor, or using any other connector configuration that allows the cannulae to be readily removed from the arbor, for example, including but not limited to, a clip, a compression seal or fitting, a quick disconnect, a twist-lock connector, or other suitable connector, wherein each connector configuration can optionally include one or more sealing elements such as a washer, gasket, O-ring, or other seal to prevent fluid leaks when connected). This allows a spacer unit to be placed between the arbor end and the cannula thereby shortening the end-to-end distance between the cannulae on the arbor. In some embodiments, the spacer has a connector configuration that is compatible with the cannulae and arbor connectors (e.g., a threaded screw or other connector configuration that allows the cannulae and spacers to be readily connected or disconnected, for example, including but not limited to, a clip, a compression seal or fitting, a quick disconnect, a twist-lock connector, or other suitable connector, wherein each connector configuration can optionally include one or more sealing elements such as a washer, gasket, O-ring, or other seal to prevent fluid leaks when connected). In some embodiments, two or more spacers can be connected end-to-end (e.g., stacked) to further shorten the end-to-end distance between the assembled cannulae on the arbor. It should be appreciated that in some embodiments a spacer has a connector configuration that is compatible with another spacer configuration so that they can be readily stacked. For example, spacers can have connector configurations that can be readily connected or disconnected (e.g., a threaded screw or other connector configuration that allows the cannulae and spacers to be readily connected or disconnected, for example, including but not limited to, a clip, a compression seal or fitting, a quick disconnect, a twist-lock connector, or other suitable connector, wherein each connector configuration can optionally include one or more sealing elements such as a washer, gasket, O-ring, or other seal to prevent fluid leaks when connected). In some embodiments, the connector configurations for connecting the spacers to each other, for connecting a space to a cannula, and/or for connecting a cannula to an arbor can be the same or similar. However, in some embodiments they are different as aspects of the disclosure are not limited in this respect.

It also should be appreciated that the spacers can be provided in different lengths (e.g., from several mm to several cm depending on the size of the reactor). In some embodiments, the spacers are up to 2 mm, up to 5 mm, 10 mm, up to 25 mm, up to 50 mm, up to 100 mm long or more. In some embodiments, the spacers are in a range of 2 mm to 10 mm, 2 mm to 50, 10 mm to 50 mm, or 10 mm to 100 mm. In some embodiments, at least one spacer is used at each end of the arbor. However, in some embodiments, a cannula unit is attached directly to each end of the arbor. The size of the organ required will dictate the number and size of inserts required.

In some embodiments, a cannula unit can have a length ranging from several mm to several cm. In some embodiments, a cannula unit has a length of about 5 mm. In some embodiments, the cannula unit has a length of up to 2 mm, up to 5 mm, 10 mm, up to 25 mm, up to 50 mm, up to 100 mm long or more. In some embodiments, the cannula unit has a length in a range of 2 mm to 10 mm, 2 mm to 50 mm, 10 mm to 50 mm, or 10 mm to 100 mm.

Accordingly, a suitable number of spacers can be selected and assembled with the cannula on the arbor in order to generate an end-to-end distance between the cannulae that is adapted for the size of the scaffold or tissue that is being attached. Typically, the end to end distance is similar to the length of the tissue or scaffold, but may be slightly shorter to avoid stretching the tissue or scaffold in some embodiments. Depending on the type of scaffold or tissue (e.g., whether it is a trachea, an oesophagus, or other tubular tissue, and whether it is for a human or an experimental model such as a mouse or rat) different lengths ranging from a several mm (e.g., around 10 mm, for example around 15 mm) to several cm (e.g., around 10 cm, around 15 cm, around 25 cm, around 50 cm, or longer or shorter) can be used.

In some embodiments, different cannula units are provided with different cannula outer diameters that are suited for different organ sizes. For example, in some embodiments different cannulae have outer diameters of about 1 mm, about 1.5 mm, about 2 mm, or about 2.5 mm. In some embodiments, cannulae have outer diameters in a range of 1 mm to 2 mm, 1 mm to 5 mm, 1 mm to 10 mm, or 2 mm to 10 mm. These can be used with scaffolds or tissues that have corresponding inner diameters. However, it should be appreciated that cannulae of other sizes (e.g., larger or smaller) can be provided depending on the intended use. In some embodiments, the outer diameter can be larger, for example 1-5 cm or larger.

It also should be appreciated that cannula and spacer units are tubular with an interior space that can have an inner diameter ranging from around 1 mm or just below 1 mm to several cms depending on the size of the cannula or spacer unit. It should be appreciated that the size of the inner diameter is defined by the outer diameter and wall thickness of the cannula or spacer units. In some embodiments, spacer units are selected to have similar inner diameters as the cannulae that they are connected to in order to avoid pressure buildup or disruption of fluid flow through the inner space leading to the inner space (the inner chamber) defined by the scaffold that is attached to the cannulae.

It should be appreciated that a scaffold can be attached to a cannula using any appropriate technique, including but not limited to, using a mechanical tether (e.g., a tie, a clip, an O-ring, an elastic element such as an elastic band of a suitable size, etc.), sutures, adhesives, or other connector or attachment means, or any combination thereof. In some embodiments, the end of a cannula is shaped to allow an end of a tubular scaffold or tissue to be secured (e.g., via a suture) to provide a tight seal (e.g., to prevent leaks). For example, the tip of the cannula may be ball-shaped or otherwise broadened relative to the neck of the cannula to allow a cylindrical scaffold or tissue end to be placed over the tip and secured with a suture (or a clamp or other securing device) placed over the narrower neck of the cannula. In some embodiments, a cannula is designed to include an end that is ribbed, tapered, or otherwise configured to help attach to an end of a scaffold (e.g., a tubular scaffold for a trachea, esophagus, or other airway region).

Figure 4:
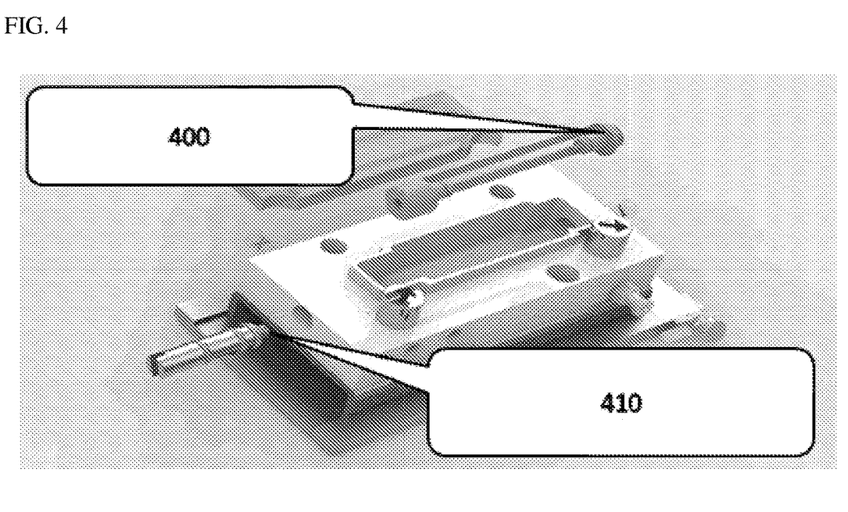
FIG. 4 illustrates a non-limiting embodiment of an arbor assembly that is aligned to be inserted into the bioreactor reservoir.

FIG. 4 illustrates a non-limiting embodiment of an arbor assembly that is aligned to be inserted into the bioreactor reservoir. Arbor assembly (400) is aligned so that the O-ring end of the assembly is inserted into the hole that is connected to the lumen flow inlet, and the driveshaft end of the assembly is inserted at the other end of the reservoir and connected to the driveshaft (400). The driveshaft can be connected by screwing the driveshaft into the arbor assembly in embodiments where the assembly and driveshaft have complementary threaded ends. However, the driveshaft and the assembly can be connected using any suitable connector as aspects of the disclosure are not limited in this respect.

FIG. 4 also shows the cover, although the cover is not shown in place on the reservoir. When in position, the cover sits loosely to allow for gas exchange. In some embodiments, there is a step-down from each of the ends of the reservoir so that the height of the ridge around the reservoir is lower in the middle allowing for gas exchange.

In some embodiments, one or more debubblers are included on the lid or a side or end wall of the reservoir.

In some embodiments, a seal wash function is provided to wash a seal on the driveshaft. A seal wash inlet and outlet are provided to allow the seal to be flushed with a solution (e.g., a non-salt solution) that prevents salt buildup on the seal (e.g., from salt in the reservoir solution). In some embodiments, a seal wash solution can be flushed through a separate space between the two outside O-rings on the driveshaft. This can prevent any buildup of evaporated salt crystals from forming on the turning shaft during long periods of use.

In some embodiments, the lumen flow inlet can be connected to a pump (e.g., a peristaltic pump) to deliver medium through the lumen.

In some embodiments, the reservoir inlet can be connected to a pump (e.g., a peristaltic pump) to deliver medium to the exterior of the scaffold or tissue in the reservoir.

However, in some embodiments, fluid flow through one or more paths can be driven by mechanical elements connected to one or more rotating elements within the bioreactor.

In some embodiments, depending on the setting of the function valve, the outlet of the lumen may change from the lumen flow outlet to the reservoir.

In some embodiments, a bioreactor described herein may include one or more additional features. For example, a bioreactor can include one or more sensors for measuring one or more of nutrient composition, nutrient concentration, dissolved oxygen concentration, dissolved carbon dioxide concentration, cell concentration, temperature, pH, and osmolality of the first fluid. Additionally or alternatively, the bioreactor may comprise one or more sensors for measuring one or more of nutrient composition, nutrient concentration, dissolved oxygen concentration, dissolved carbon dioxide concentration, cell concentration, temperature, pH, and osmolality of the second fluid. In some cases, a first and/or second sensor is adapted to measure shear stress or flow rate.

In some embodiments, a gas monitoring system can be used in conjunction with the bioreactor described herein. In some embodiments, one or more sensors that provide for the measurement of $CO_2$, $O_2$, pH, and/or humidity of the system can be placed in line on the reservoir outlet flow. In some embodiments, oxygen consumption rate (OCR) can be monitored by placing a flow through oxygen sensor in the lumen of the flow inlet line. However, it should be appreciated that these sensors can be positioned at other locations as aspects of the disclosure are not limited in this respect. In some embodiments, one or more sensors that provide for the measurement of $CO_2$, $O_2$, pH, and/or humidity of the system can be included within the bioreactor (e.g., attached to, integral to, or otherwise connected to an internal wall or lid of the bioreactor).

In some embodiments, one or more heating or cooling elements can be incorporated within the bioreactor (e.g., on an inner surface of the reservoir or lid, and/or integrated within one or more of the walls and/or the base of the reservoir, for example in a Teflon base).

In some embodiments, one or more air or oxygen sources, carbon filters, and/or one or more humidification or dehumidification systems are connected to the bioreactor and configured to control the level of oxygen, carbon dioxide, and/or humidity within the bioreactor (e.g., in response to signals from the one or more detectors in or attached to the bioreactor). In some embodiments, one or more controllers are attached to the sensors and other systems to control the internal environment of the bioreactor.

In some embodiments, the bioreactor can be sealed (e.g., the lid of the bioreactor can be sealed onto the reservoir) in a configuration that allows the bioreactor to act as a self-contained incubator without needing to place the bioreactor inside a larger incubator.

In some embodiments, a bioreactor can include one or more light sources (e.g., incandescent, LED, or other light source). These can be placed within the bioreactor to illuminate the scaffold and cells or tissue that are grown on the scaffold. In some embodiments, the scaffold can be monitored using a camera or other light sensitive device that can be placed within or outside the bioreactor. In some embodiments, the bioreactor includes a window that allows visible light or other light wavelengths from within the bioreactor to be detected by a camera or other light sensitive device placed outside the bioreactor. In some embodiments, the inner surface of the window can be wiped from the inside to prevent liquid droplets (e.g., due to the humid air inside the bioreactor) from accumulating on the inner surface and interfering with the monitoring of the scaffold and or cells or tissue growing on the scaffold. In some embodiments, the surface can be wiped by a wiper that is connected (e.g., mechanically connected) to the rotating scaffold, scaffold holder, arbor, arbor drive, or other rotating component. In some embodiments, an encoder on a rotating component of the bioreactor (or on the motor or other system that is driving rotation of the scaffold) can be used to synchronize the light information that is detected by the camera or other light sensitive device with the rotation of the scaffold. In some embodiments, this allows information about the cell or tissue growth or health based on light information (including for example infrared light information) from different portions of the scaffold to be mapped and monitored. In some embodiments, this allows for decellularization of a natural scaffold (for example based on the loss of a light signal associated with cellularized tissue) to be monitored and evaluated.

In some embodiments, a bioreactor described herein also may include one or more stimulation plates that can be used to stimulate (e.g., electrically) the scaffold/engineered organ.

In operation, decellularization and/or recellularization medium can be flowed through the lumen and/or through the reservoir of the bioreactor depending on the desired use.

In some embodiments the cover may be sealed on to the reservoir. In some embodiments, a sealed bioreactor can be a self-contained incubator as described herein. In some embodiments, a sealed bioreactor can be pressurized or put under vacuum to assist with cell growth and/or decellularization depending on the application.

Decellularization

In some embodiments, a bioreactor described herein can be used for decellularization wherein a natural tissue (e.g., a trachea or the airway) is attached to the cannulae at each end of the arbor and one or more decellularization media are used to remove cells from the tissue thereby exposing a natural scaffold. One or more decellularization media can be placed in one or more external reservoirs and/or introduced (e.g., pumped) through the lumen of the tissue and/or into the bioreactor reservoir using appropriate function valve settings. If the identical reagent is to be used for both the lumen and the bioreactor reservoir, a Y fitting may be placed inline along with tubing connecting to both the intra-lumen and extra lumen inlet ports.

Recellularization

In some embodiments, a bioreactor described herein can be used for recellularization wherein a natural or synthetic scaffold is attached to the cannulae at each end of the arbor and one or more recellularization media are used to promote cell growth and/or differentiation on the scaffold (e.g., after the scaffold has been seeded with cells). One or more recellularization media can be placed in the reservoir and/or introduced (e.g., pumped) through the lumen of the tissue using appropriate function valve settings.

One or more channels of the bioreactor (e.g., intralumenal and/or extralumenal) can be connected to an external reservoir (e.g., a bottle) using tubing or other fluid connectors.

It should be appreciated that the same or different recellularization media can be used for the intraluminal and extra-luminal flow paths of the organ. If the identical medium is to be used, a Y fitting may be placed inline and the tubing from the same reservoir is connected to both the intra-lumen and extra lumen inlet ports. However, it should be appreciated that independent reagents can be used for the intra-luminal versus the extra luminal flow paths, for example by connecting separate reservoirs to the different inlet ports.

In some embodiments, a single medium may be used for both the intralumenal and extralumenal flow paths. However, in some embodiments, for example when particular additives or factors (e.g., growth factors and/or cytokines) are used on the intralumenal side, they can be recirculated and separate external intralumenal and extralumenal reservoirs can be used.

Cell Seeding

In some embodiments, one or more of the following acts can be taken to prepare a scaffold for cell seeding. In some embodiments, the bioreactor can be washed (e.g., with PBS, prior to installing the scaffold. In some embodiments, the components can be washed by running the bioreactor (e.g., at about 5 rpm) with a wash solution in the reservoir.

In some embodiments, a scaffold can be washed and conditioned in culture medium prior to cell seeding. In some embodiments, the scaffold is attached to the arbor (e.g., to the cannulae at both ends of the arbor assembly, and incubated with culture medium in the bioreactor reservoir (e.g., rotating at about 2 rpm for about 2 hours).

Appropriate fluid path and reservoir settings can then be selected and the reservoir can be filled with an appropriate level of growth medium.

In some embodiments, a cell inoculum (e.g., a cell suspension) is added to the surface of the scaffold. The seeded scaffold on the bioreactor can then be placed in a cell incubator. In some embodiments, the incubator is maintained at 37° C. and 5% carbon dioxide atmosphere. In some embodiments, the bioreactor is set to rotate at about 2 rpm.

Sterilization

In some embodiments, one or more articles of a bioreactor can be sterilized using any suitable technique (e.g., autoclaving, plasma sterilization, EtO gas sterilization, etc.). In some embodiments, the components of the reactor are constructed from material that can be sterilized as described herein. For example, the reservoir can be a PTFE (e.g., material available under the name Teflon) block; the baseplate, driveshaft, and valves can be steel components; rubber O-rings can be silicone components, luer fittings can be made of polyvinylidene fluoride or PVDF (e.g., material available under the name Kynar), arbor components can be made of polyether ether ketone or PEEK, and the cover can be polycarbonate. However, it should be appreciated that other materials (e.g., other metallic, plastic, or other polymeric materials) can be used.

Figure 5:
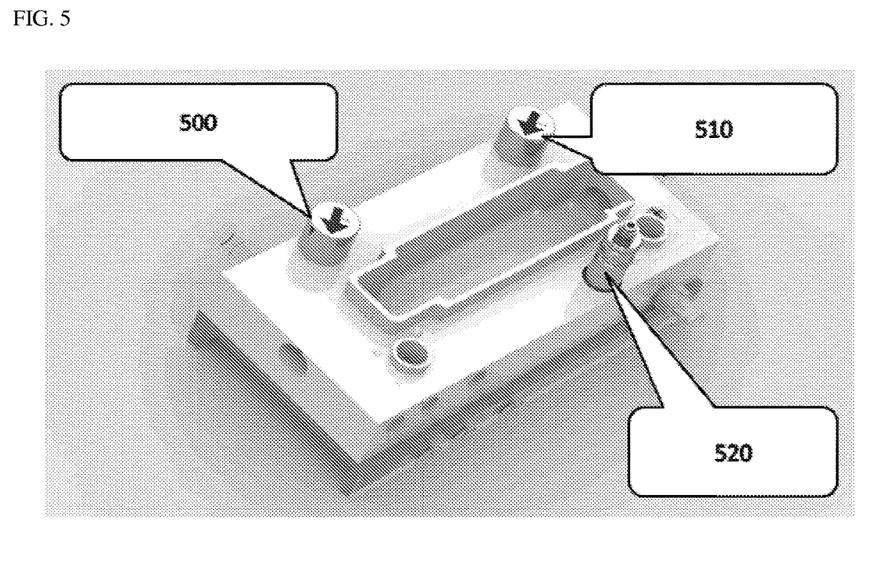
FIG. 5 illustrates a non-limiting embodiment where the driveshaft and valve are removed from the reservoir block prior to sterilization.

In some embodiments, one or more components can be disassembled prior to sterilization. FIG. 5 illustrates a non-limiting embodiment where the driveshaft and valve are removed from the reservoir block prior to sterilization. FIG. 5 illustrates a non-limiting embodiment of hole features that prevent component loss during sterilization. The function valve can be removed and stored as shown in (500) during sterilization. The level valve can be removed and stored as shown in (510) during sterilization. The driveshaft can be removed and stored as shown in (520) during sterilization. In this example, the block includes holes for storing these components during sterilization. However, these are not required as aspects of the disclosure are not limited in this respect.

In some embodiments, after sterilization a bioreactor can be placed in a laminar flow hood or other sterile environment for assembly to reduce contamination.

Fluid Flow

In some embodiments, fluid flow is promoted by pumps connected to reservoirs, fluid passages, and/or conduits within the bioreactor or attached to the bioreactor. In some embodiments, fluid flow is promoted by a mechanical force (for example driven by rotation of the arbor attachment). In some embodiments, the arbor itself, or the rotating drive shaft, or other rotating element is connected to one or more paddles, cups, or other shaped elements that promote fluid movement (e.g., flow through one or more pathways and/or distribution over the scaffold or over cells or tissue growing on the scaffold).

Figure 6A:
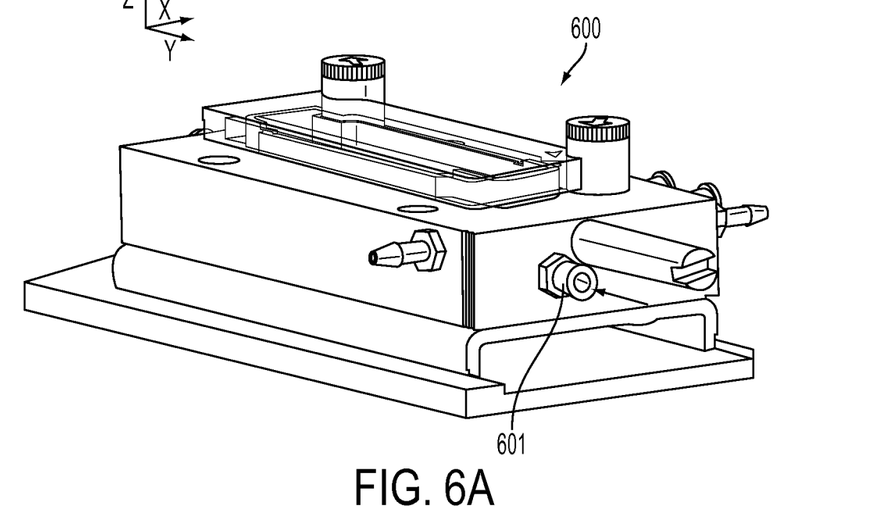
FIG. 6A is a perspective view of a non-limiting embodiment of a bioreactor reservoir.
Figure 6B:
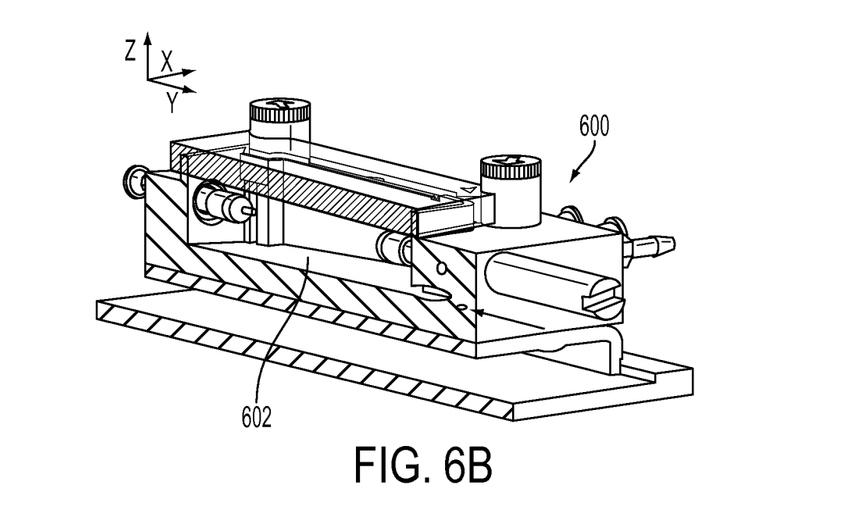
FIG. 6B is a cut-away perspective view of a non-limiting embodiment of a bioreactor reservoir.
Figure 6C:
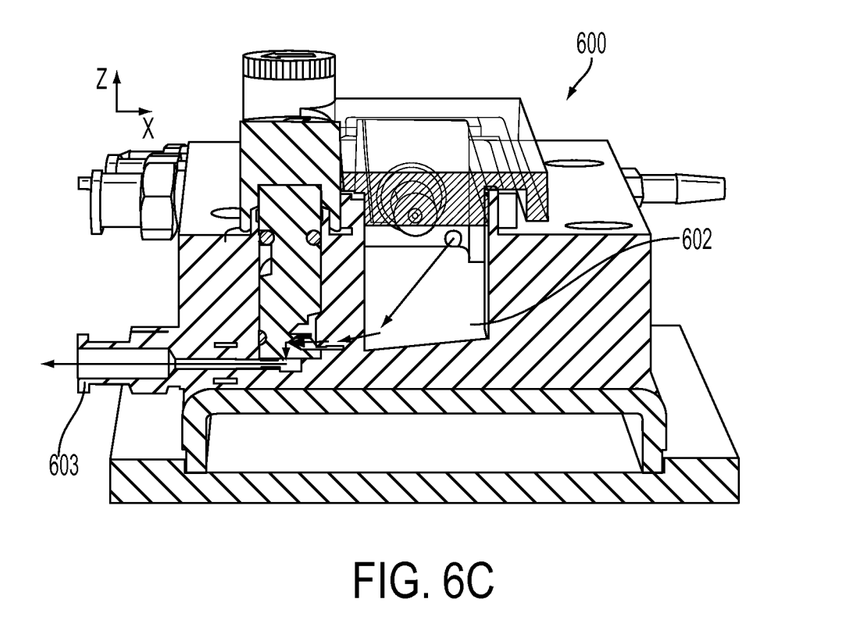
FIG. 6C is a cut-away side view of a non-limiting embodiment of a bioreactor reservoir (arrows depict direction of fluid flow).

In some embodiments, a reservoir of a bioreactor is shaped to promote fluid flow in one or more directions. In some embodiments, the shape of the inner surface of the base of the bioreactor is configured (e.g., sloped, inclined, or otherwise shaped) to cause fluid (and/or cellular material or debris that is deposited at the bottom of the reservoir) to flow towards one or more points (e.g., low points). In some embodiments, one or more passages or conduits are connected to each low point. These can be useful, for example, to remove material (e.g., cellular material) and either recirculate it, discard it, analyze it, or any combination thereof. FIGS. 6A-C illustrates a non-limiting embodiment of a reservoir 600 configured for containing a culture media and for accepting an arbor assembly that is rotatable in the culture media. The reservoir 600 is configured with a fluid inlet 601 adapted for permitting fluid (e.g., culture media) to be supplied to the reservoir 600. The reservoir 600 is also configured with a fluid outlet 603 adapted for permitting fluid to exit the reservoir 600. In some embodiments, a fluid (e.g., culture media) can be continuously circulated through the reservoir 600 from the fluid inlet 601 to the fluid outlet 603. In some embodiments, a fluid (e.g., culture media) can be supplied to the reservoir 600 through the fluid inlet 601, maintained in the reservoir 600 for a period of time, and then removed from the reservoir 600 through the fluid outlet 602. For example, a fluid may be supplied to the reservoir and maintained in the reservoir (without being removed through the fluid outlet 603) for up to 30 min., 1 hr., 2 hrs., 4 hrs., 8 hrs., 12 hrs., 16 hrs., 18 hrs., 24 hrs., 48 hrs. or more.

As shown in FIGS. 6B and 6C, the lower surface 602 of the reservoir is sloped from the fluid inlet 601 to the fluid outlet 603. In some embodiments, the sloped lower surface 602 is advantageous because it facilitates fluid flow between the fluid inlet 601 and fluid outlet 603. In some embodiments, the sloped lower surface 602 is advantageous because it reduces the extent to which cells and other materials present in fluid (e.g., culture media) within the reservoir 600 collect at the bottom of the reservoir 600 (e.g., at or near the middle of the reservoir). Instead, because of the sloped bottom, cells and other materials tend to move under force of gravity down the slope and collect at or near the fluid outlet 603. Thus, when fluid is transferred out through the fluid outlet 603 the cells and other materials are readily drawn out from the reservoir 600.

Materials

It should be appreciated that different materials (e.g., including metal, plastic, rubber, a range of different polymers, printed material, for example 3-D printed material, or any combination thereof) can be used to manufacture different components of a bioreactor as described herein. It should be appreciated that in some embodiments, all or most components are manufactured in a material that is resistant to autoclaving. It also should be appreciated that in some embodiments, all or more components are compatible with an MRI device (for example the are non-metallic, non-magnetic, or non-paramagnetic). Accordingly, in some embodiments, one or more valve, connector, and other components are manufactured using one or more MRI compatible materials. In some embodiments, one or more of the reservoir, lid, arbor, drive shaft, and other components of a bioreactor described herein are manufacture using one or more MRI compatible materials.

It should be appreciated that different configurations can be used for different tissue and organ types. It should be appreciated that these principles may be applied to other organ or tissue scaffolds.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The following publications are incorporated herein by reference in their entireties for all purposes: International Patent Application Publication Serial Number WO2013/163358, which published on a Oct. 31, 2013 and is entitled, ENGINEERED TISSUE SCAFFOLDS AND SUPPORTS THEREOF; International Patent Application Publication Serial Number WO 2011/034627, which published on a Mar. 24, 2011 and is entitled, METHODS AND APPARATUS FOR INTRODUCING CELLS AT A TISSUE SITE; International Patent Application Publication Serial Number WO 2011/062621, which published on a May 26, 2011 and is entitled, BIOREACTORS, SYSTEMS, AND METHODS FOR PRODUCING AND/OR ANALYZING ORGANS; International Patent Application Publication Serial Number WO 2013/110021, which published on a Jul. 25, 2013 and is entitled, METHOD FOR EVALUATING TISSUE INJURIES; International Patent Application Publication Serial Number WO 2013/155488, which published on a Oct. 17, 2013 and is entitled, ELASTIC SCAFFOLDS FOR TISSUE GROWTH; International Patent Application Publication Serial Number WO 2014/004746, which published on a Jan. 3, 2014 and is entitled, METHODS AND COMPOSITIONS FOR PROMOTING THE STRUCTURAL INTEGRITY OF SCAFFOLDS FOR TISSUE ENGINEERING; International Patent Application Serial Number PCT/US 13/52437, which was filed on Jul. 28, 2013 and entitled ANALYTICAL METHODS; International Patent Application Serial Number PCT/US14/10941, which was filed on Jan. 9, 2014.

What is claimed is:

1. A bioreactor arbor assembly comprising:
   a first cylindrical end unit and a second cylindrical end unit, the first cylindrical end unit and the second cylindrical end unit each having an outer arcuate surface and a planar face connected to the outer arcuate surface, wherein the planar faces of the first and second cylindrical end units confront one another and are connected via at least one elongate connecting shaft, the elongate shaft attached to a region defined on the outer arcuate surface of the respective first cylindrical end unit and the second cylindrical end unit, e,
   a first cannula unit connected to the first cylindrical end unit,
   a second cannula unit connected to the second cylindrical end unit, wherein the second cannula unit is connected via threaded screws onto the second cylindrical end unit, either directly or indirectly, and
   a spacer unit positioned between the first cannula unit and the planar face of the first cylindrical end unit, wherein the first cannula unit comprises an orifice and the second cannula unit comprises an orifice, wherein the first and second cannula units are arranged such that they confront one another along a longitudinal axis that passes through the two orifices.

2. The arbor assembly of claim 1, wherein a spacer unit is positioned between the second cannula unit and the second cylindrical end unit.

3. The arbor assembly of claim 2, wherein a first opening of a tubular scaffold is attached to the first cannula unit and a second opening of a tubular scaffold is attached to the second cannula unit.

4. A bioreactor comprising a reservoir and the arbor assembly of claim 1.

5. A bioreactor arbor assembly comprising:
   a first cylindrical end unit and a second cylindrical end unit, wherein the first and second end units confront one another and are connected via an elongate shaft,
   a first cannula unit connected to the first cylindrical end unit, and
   a second cannula unit connected to the second cylindrical end unit, wherein a first opening of a tubular scaffold is attached to the first cannula unit and a second opening of a tubular scaffold is attached to the second cannula unit, wherein the second cannula end unit is connected to the second end unit, wherein a spacer unit is positioned between the first cannula unit and the first cylindrical end unit end and wherein the first cannula unit comprises an orifice and the second cannula unit comprises an orifice, wherein the first and second cannula units are arranged such that they confront one another along a longitudinal axis that passes through the two orifices.

6. A bioreactor comprising a reservoir and the arbor assembly of claim 5.

* * * * *